United States Patent [19]
Bodor et al.

[11] Patent Number: 4,952,687
[45] Date of Patent: Aug. 28, 1990

[54] FATTY ACID ESTERS OF SUGARS AND SUGAR ALCOHOLS

[75] Inventors: Janos Bodor, Rijswijk; Geoffrey Page, Palmerston North, both of New Zealand

[73] Assignee: Lever Brothers Company, New York, N.Y.

[21] Appl. No.: 87,005

[22] Filed: Aug. 18, 1987

Related U.S. Application Data

[63] Continuation-in-part of Ser. No. 14,963, Feb. 17, 1987, abandoned.

[30] Foreign Application Priority Data

Feb. 19, 1986 [NL] Netherlands ............. 8600415

[51] Int. Cl.$^5$ ............................................. C07H 13/06
[52] U.S. Cl. .................................... 536/119; 536/115; 426/321; 426/602; 426/612; 514/23; 514/42; 514/53
[58] Field of Search ............ 536/115, 119; 426/321, 426/611, 612, 602; 514/23, 42, 53

[56] References Cited

U.S. PATENT DOCUMENTS

| | | | |
|---|---|---|---|
| 3,093,481 | 6/1963 | Eckey et al. | 426/321 |
| 3,158,490 | 11/1964 | Baur et al. | 426/612 |
| 3,600,186 | 8/1971 | Mattson et al. | 426/611 |
| 3,954,976 | 5/1976 | Mattson et al. | 514/23 |
| 3,963,699 | 6/1976 | Rizzi et al. | 426/611 |
| 4,005,195 | 1/1977 | Jandacek | 514/23 |
| 4,005,196 | 1/1977 | Jandacek et al. | 514/23 |
| 4,034,083 | 7/1977 | Mattson | 514/53 |
| 4,241,054 | 12/1980 | Volpenhein et al. | 514/42 |
| 4,264,583 | 4/1981 | Jandacek | 514/23 |
| 4,275,081 | 6/1981 | Coleman et al. | 426/33 |
| 4,368,213 | 1/1983 | Hollenbach et al. | 426/590 |
| 4,382,924 | 5/1983 | Berling | 514/53 |
| 4,446,165 | 5/1984 | Roberts | 426/602 |
| 4,517,360 | 5/1985 | Volpenhein | 536/124 |
| 4,518,772 | 5/1985 | Volpenhein | 536/119 |

FOREIGN PATENT DOCUMENTS 062565 10/1982 European Pat. Off.
69412 1/1983 European Pat. Off.

OTHER PUBLICATIONS

Jandacek et al., "Physical Properties of Pure Sucrose Octaesters," *Chem. & Phys. Lipids*, vol. 22 (1978), pp. 163–176.

*Bailey's Industrial Oil and Fat Products*, 3rd Ed. (1964), pp. 88–89, 93–95, 811, 893, 1053–1054, 1059–1062.

Fieser et al., *Advanced Organic Chemistry* (1961), p. 990.

Sims et al., "Formation of Trans Isomers During the Hydrogenization of Glyceride Oils", *J. Am. Oil Chem. Soc.*, vol. 30 (1953), pp. 410–413.

Allen et al., "Isomerization During Hydrogenation: Oleic Acid", *J. Am. Oil Chem. Soc.*, vol. 32 (1955), pp. 400–405.

Litchfield et al., "Cis–Trans Isomerization of Oleic, Linoleic and Linolenic Acids," *J. Am. Oil Chem. Soc.*, vol. 40 (1963), pp. 553–557.

Griffiths et al., "The Interconversion of Cis– and Trans– Modification of Monoethylenic Higher Fatty Acids by Nitrogen Trioxide (the 'Elaidin Reaction')," *J. Chem. Soc.* (1932), pp. 2315–2324.

Feuge et al., "Modification of Vegatable Oils: the Formation of Trans Isomers During the Hydrogenation of Methyl Oleate and Triolein", *J. Am. Oil Chem. Soc.*, vol. 28 (1951), pp. 420–426.

Hastert, "Practical Aspects of Hydrogenation and Soybean Salad Oil Manufacture," *J. Am. Oil Chem. Soc.*, vol. 58 (1981), pp. 169–174.

"Bailey's Industrial Oil and Fat Products", edited by D. Swern 3 (1964) 88–89 and 1053–1054.

*Primary Examiner*—Ronald W. Griffin
*Attorney, Agent, or Firm*—Gerard J. McGowan, Jr.

[57] ABSTRACT

The oxidative stability of esters of unsaturated fatty acids and polyols having from 4–8 hydroxyl groups, preferably of sugars or sugar alcohols, more preferably of sucrose, is improved if the esters contain an effective amount of the trans-unsaturated fatty acid chains.

If more than 50% of the hydroxyl groups of the polyols are esterified, the esters can be used as low-calorie fat replacers, which in the case of sucrose with at least 4 hydroxyl groups esterified are called SPE (sucrose polyesters). If only 1–3 hydroxyl groups are esterified, the esters can act as emulsifiers.

The ratio of cis:trans double bonds preferably ranges from (20:80) to (40:60), more preferably from (30:70) to (35:65). The trans-unsaturated fatty acid esters of polyols can be used in an amount of 0.5–99% of an edible composition, either as an emulsifier or as a fat replacer.

29 Claims, No Drawings

FATTY ACID ESTERS OF SUGARS AND SUGAR ALCOHOLS

This is a continuation-in-part application of copending U.S. application Ser. No. 014,963, now abandoned.

The present invention relates to fatty acid esters, in particular fatty acid polyesters of sugars and sugar alcohols (SPE). Such polyesters are known. Their preparation is described in, for example, U.S. Pat. Nos. 3,963,699 (G.P. Rizzi & H.M. Taylor), 4,517,360 (R.A. Volpenhein) and 4,518,772 (R.A. Volpenhein) and European patent specification 0 062 565 (Blohorn S.A.).

In general the SPE derived from saturated fatty acids with 12 or more carbon atoms are solid and the SPE derived from unsaturated fatty acids are liquid at ambient temperature.

In U.S. No. 3,600,186 (F.H. Mattson & R.A. Volpenhein) the use is described of SPE having at least 4 fatty acid moieties per sugar or sugar alcohol moiety as low calorie fats in cooking and salad oil.

The use of SPE in fat-containing compositions is also described in U.S. Pat. Nos. 4,005,195 (R.J. Jandacek), 4,005,196 (R.J. Jandacek & F.H. Mattson), 4,034,083 (F.H. Mattson), 4,241,054 (R.A. Volpenhein & R.J. Jandacek), 4,264,583 (R.J. Jandacek), 4,382,924 (K.G. Berling & T.G. Crosby), and 4,446,165 (B.A. Roberts), whereas their use in a dietary beverage emulsion is described in U.S. Pat. No. 4,368,213 (E.J. Hollenbach & N.B. Howard).

The above-mentioned patent specifications are incorporated herein by reference. In particular, U.S. Pat. Nos. 4,005,195 and 4,005,196 relate to the addition of anti-anal leakage agents to polyol fatty acid polyesters liquid at body temperature, i.e. at about 37° C. It is stated that these agents can avoid anal leakage problems caused by the consumption of liquid polyesters. In these patents, $C_{12-24}$ saturated fatty acids or salts thereof, precursors of these $C_{12-24}$ fatty acids such as ingestible digestible esters of these fatty acids, e.g. lower alkyl esters and triglycerides, as well as polyol fatty acid polyesters solid at body temperature are disclosed as examples of anti-anal leakage agents.

Further, U.S. Pat. Nos. 4,005,196 and 4,043,083 relate to the addition of fat-soluble vitamins A, D, E or K, or mixtures thereof to polyol fatty acid polyesters. It is stated in these patents that this addition can avoid problems which might occur if ingestion of polyol fatty acid polyesters interfere with the body's uptake of fat-soluble vitamins.

In this specification by "sugars and sugar alcohols" is meant a group of polyols having from 4 to 8 hydroxyl groups. Examples of preferred polyols are sugars, including monosaccharides and disaccharides, and sugar alcohols as well as derivatives thereof having from 4 to 8 hydroxyl groups.

Examples of monosaccharides having 4 hydroxyl groups are arabinose, ribose and xylose. An example of a sugar alcohol having 4 hydroxyl groups is the sugar alcohol derived from erythrose, i.e. erythritol.

Examples of monosaccharides having 5 hydroxyl groups are galactose, fructose, glucose and sorbose. An example of a sugar alcohol having 5 hydroxyl groups is the sugar alcohol derived from xylose, i.e. xylitol.

Examples of sugar alcohols having 6 hydroxyl groups are those derived from glucose and sorbose as well as from the hydrolysis products of sucrose, e.g. sorbitol and mannitol.

Examples of disaccharides are maltose, lactose and sucrose, the latter being preferred, all of which contain 8 hydroxyl groups.

Another example of a polyol having 4 hydroxyl groups is alpha-methyl glucoside (=alpha-methyl ether of glucose) which in fact is a sugar derivative.

As described in the above-mentioned publications, it is desirable that for polyesters being substantially non-digestible by human beings at least 4 hydroxyl groups are esterified. These non-digestible polyesters are not absorbed by the human body and therefore suitable for use in low-calorie compositions.

For many applications, including margarines and other fat spreads as well as cooking oils, the oxidative stability can be a limiting factor for practical use. In particular oxidative rancidity can occur with fat and oil products, which rancidity is formed via intermediates like peroxides leading to breakdown products of which aldehydes and ketones are the most important for the organoleptic quality of the fat product.

It is customary to use antioxidants in oil and fat products containing triacylglycerols (=triglycerides) based on natural fatty acids, both in pure and partially hydrogenated form to avoid autoxidation of the double bonds in the fatty acids radicals present in the oil and fat products. It has now been found that the oxidation stability of SPE containing unsaturated fatty acid residues can be improved by providing the SPE with an effective amount of trans-unsaturated fatty acid chains. The fatty acid chains in the SPE can be derived from triacylglycerols or the corresponding fatty acids or lower alkyl esters thereof, which are hydrogenated under isomerizing conditions. Trans-hardened oils such as soybean oil and rapeseed oil which after trans-hardening have a melting point of about 36° C. are preferred as fatty acid starting materials for the preparation of the SPE. Alternatively, the trans-hardening can be carried out with SPE-containing cis-mono- or cis-polyunsaturated fatty acid chains as a starting material.

The polyesters according to the invention preferably have a ratio of cis:trans double bonds ranging from (20:80) to (40:60), more preferably from (30:70) to (35:65). Good results were obtained with polyesters in which the ratio of cis:trans double bonds was that belonging to the thermodynamic equilibrium obtained by hydrogenating, under isomerising conditions which are known to the man skilled in the art of fat chemistry (see for example Bailey's Industrial Oil and Fat Products, Edited by D.Swern 3 (1964) 88–89 and 1053–1054).

The effective amount can be determined by simple experiments using an accelerated oxidation test, whereby the product is subjected to aeration at a temperature of about 100° C. Such a test can be carried out by an equipment marketed under the name of Rancimat ® by the firm Metrohm A.G., Herisau (Switzerland).

For the determination of the oxidative stability of oils and fats several methods have been developed in the past. One of these methods is the so-called Swift test. In this test a sample of oil is kept at about 100° C. and at regular intervals the peroxide value is determined. The Induction Period (IP) is the time required for the Peroxide value to reach an arbitrary value: for animal fats 20 and for vegetable fats 100 meq. oxygen per kg of fat. Since this method was labour-intensive and time-consuming, an automated version of the test was developed: the Rancimat. With the Rancimat the end of the IP is determined by the rise in conductivity of water, in which air is entrapped that has passed through the heated fat, thus carrying over low molecular weight acids, mainly formic acid, formed as breakdown product of peroxides. Rancidity itself is not measured with this test, because rancidity is only to be experienced organoleptically. However, good correlation has been found between flavour scores as determined by a panel and the I.P. determined with the Rancimat, for example for groundnut oil heated for 20 hours at 100° C. with samples for analysis being taken every 2 hours.

In practice, both the Swift test and the determination of the Induction Period with the Rancimat give a good indication for the oxidative stability of an oil or fat under normal use conditions, both at ambient temperature and at cooking and frying temperatures.

It is preferred that the SPE have a Rancimat value of at least 20 hours, more preferably at least 30 hours.

The following Table gives some values determined with the Rancimat test (I.P. $^{100}$ in hours).

TABLE

| Polyol | Fatty acid type | Induction period | Melting point |
|---|---|---|---|
| | | Saturated | |
| s | BO65 | at least 70 [1] | 60+ |
| s | PK39 | at least 70 [1] | 22.5 |
| s | PO58 | at least 70 [1] | n.d. |
| s [2] | (1:3 w/w) PK39/PO58 | at least 70 [1] | 48.5 |
| g | AR [3] | at least 70 [1] | 60+ |
| | | Cis-unsaturated | |
| s | AR | 2–7 | liquid at room temp. |
| s | BO | less than 1 | |
| s | MZ | 1 | |
| s | OV | 2–3 | |
| s | SF | less than 1 | |
| g | AR | less than 1 | |
| | | Mainly trans-unsaturated | |
| s | BO36 | at least 90 [1] | 22.7 |
| s | RP36 | 36 | 24.7 |
| s [4] | BO36/PO58 (1:2 w/w) | at least 115 [1] | 49.5 |
| s [4] | BO36/PO58 (1:1 w/w) | 80 | 43.0 |
| s [4] | BO36/PO58 (2:1 w/w) | at least 115 [1] | 38.7 |
| g | BO36 | at least 95 [1] | 20.5 |

[1] After the hours given the experiment was interrupted; the oil was still stable at that time.
[2] Saccharose fatty acid polyesters derived from a mixture of methyl esters of fatty acids derived from fully hydrogenated palmkernel oil (PK39) and fully hydrogenated palm oil (PO58).
[3] The arachidic oil fatty acids polyester of alpha-methyl glucoside was fully hydrogenated.
[4] Saccharose fatty acid polyesters derived from a mixture of methyl esters of fatty acids derived from trans-hardened soybean oil (BO36) and fully hydrogenated palm oil (PO58).
Polyol: s = Saccharose (= sucrose)
Polyol: g = Alpha-methyl glucoside (= alpha-methyl ether of glucose)
The fatty acid type "saturated" means fatty acids derived from fully hydrogenated triglyceride oils, e.g. soybean oil (BO65), palmkernel oil (PK39) and palm oil (PO58). The numbers give the slipmelting point of the hardened oils.
RP36 = Rapeseed oil trans-hardened to a melting point of 36° C.
BO36 = Soybean oil trans-hardened to a melting point of 36° C.
AR = Arachidic oil
BO = Soybean oil
MZ = Maize oil
OV = Olive oil
SF = Sunflower oil The Table shows that SPE's from saccharose and alpha-methyl glucoside containing fully hydrogenated fatty acids have a high oxidative stability (Rancimat figures of more than 70 hours), whereas those polyesters of unhardened fatty acids derived from natural oils (fatty acid type "cis-unsaturated") have a poor oxidative stability (Rancimat figures of less than 1 up to 7 hours).

The SPE's from saccharose and alpha-methyl glucoside containing trans-hardened oils (fatty acid type "mainly trans-saturated") also have a good oxidative stability (Rancimat figures of 36 up to more than 115 hours). This good oxidation stability is considered surprising, since these polyesters, which are all liquid or semi-liquid at body temperature, still contain a relatively high proportion of unsaturated fatty acid radicals.

In the SPE's mentioned in the Table at least 75% of the hydroxyl group are esterified.

The SPE according to the invention having a high degree of esterification, e.g. SPE of which at least 50% or more than 70% or even more than 80% of the hydroxyl groups are esterified with fatty acids are preferred, since they can be used in food compositions or pharmaceutical compositions for decreasing the blood cholesterol level in human beings.

In order to improve the properties of the SPE as a fat substitute it is desirable that the fatty acid chains have at least 6 carbon atoms, preferably at least 8 carbon atoms and more preferably at least 10 carbon atoms. For practical purpose the fatty acid chains have at most 24 carbon atoms, preferably at most 20 carbon atoms. When natural oils and fats are used as starting materials for the fatty acids the latter have usually chains of from 12 to 22 carbon atoms.

The invention further provides the use of the SPE according to the invention in edible compositions containing 0.5–99 wt. %, preferably 10–99 wt. %, more preferably 30–80 wt. % of SPE according to the invention, the balance consisting of edible matter. Examples of such compositions are edible fat products suitable as a bread spread, e.g. butter, margarine or mixtures thereof (so-called "melange" products) and low-calorie substitutes therefor having a fat content of about 20 to about 60 wt. %, as a mayonnaise-type product having a fat content of about 20 to about 80 wt. %, as a baking, cooking or frying product, for example a shortening or frying oil, as a dairy-based product, e.g. cheese, cream, and yoghurt products, as a whipped product such as ice-cream or whipped non-dairy cream, as a salad oil, or as pharmaceutical carrier.

If the polyesters are used in food products, one may also use one or more oil-soluble vitamins, such as vitamin A, D, E or K, to avoid the above-indicated vitamin deficiency, as well as use one or more antianal leakage agents, such as $C_{12-24}$ fatty acids, derivatives or precursors thereof, or solid polyol fatty acid polyesters, to avoid the potential anal leakage problems following ingestion of liquid polyol fatty acid polyesters as described above. However, it is not yet clear that these effects occur under practical conditions when people have a normal diet in which only part of the triglycerides is replaced by polyol fatty acid polyesters. Often, in a normal diet, other food ingredients also contain oil-soluble vitamins, as well as fats containing saturated fatty acid residues acting as anti-anal leakage agents.

Although the invention was mainly illustrated with sugar polyesters, the beneficial effect of the transunsaturated fatty acid residues can also be obtained when used in sugar esters containing only one, two or three fatty acid residues. Such sugar esters having a lower degree of esterification can be applied as emulsifiers, e.g. in the food industry. The lower part of the ranges given in the previous paragraph is of importance when the sugar ester is used as an emulsifier, whereas the upper part of the ranges is important when the sugar ester is used as a low-calorie fat substitute.

We claim:
1. Fatty acid esters of sugar or sugar alcohols, said sugars and sugar alcohols being polyols having from 4 to 8 hydroxyl groups, said esters comprising unsatu- rated fatty acid residues, containing a ratio of cis:trans double bonds of from 20:80 to 40:60.

2. Esters according to claim 1, of which at least 50% of the hydroxyl groups are esterified with fatty acids.

3. Esters according to claim 2, in which the degree of esterification is so high that the polyester is substantially non-digestible by human beings.

4. Esters according to claim 2, of which at least 70% of the hydroxyl groups are esterified with fatty acids.

5. Esters according to claim 4, of which at least 80% of the hydroxyl groups are esterified with fatty, acids.

6. Esters according to claim 1, in which the sugar or sugar alcohol residue is a sucrose residue.

7. Esters according to claim 1, comprising fatty acid chains having at most 24 carbon atoms.

8. Esters according to claim 7, wherein said fatty acid chains have from 12–22 carbon atoms.

9. Esters according to claim 1, comprising esters derived from an oil trans-hardened to a melting point of about 36° C. selected from the group consisting of trans-hardened rapeseed oil and trans-hardened soybean oil.

10. Esters according to claim 1, comprising an amount of trans-fatty acids such that the product has a stability of at least 20 hours in the Rancimat wherein the product is subjected to aeration at a temperature of about 100° C.

11. Esters according to claim 10, comprising an amount of trans-fatty acids such that the product has a stability of at least 30 hours in the Rancimat wherein the product is subjected to aeration of a temperature of about 100° C.

12. Esters according to claim 1, comprising fatty acid chains having at least 8 carbon atoms.

13. Esters according to claim 12, comprising fatty acid chains having at least 10 carbon atoms.

14. Esters according to claim 1, comprising fatty acid chains having at most 20 carbon atoms.

15. Esters according to claim 1, having a ratio of cis:trans double bonds ranging from (35:65) to (30:70).

16. Fatty acid esters according to claim 1, wherein the esters are liquid or semiliquid.

17. Fatty acid esters according to claim 16, wherein the esters are liquid.

18. Fatty acid esters according to claim 16, wherein the esters are semiliquid.

19. The esters according to claim 16 wherein at least 50% of the hydroxyl groups are esterified with fatty acids.

20. The esters according to claim 19 comprising fatty acid chains including from 8 to 24 carbon atoms.

21. The esters according to claim 16 in which the sugar or sugar alcohol residue is a sucrose residue.

22. The esters according to claim 16 comprising fatty acid chains including from 8 to 24 carbon atoms.

23. The esters according to claim 16 comprising an amount of trans-fatty acids such that the product has a stability of at least 20 hours in the Rancimat wherein the product is subjected to aeration at a temperature of about 100° C.

24. A composition containing 0.5–99 wt. % of esters according to claim 1, the balance consisting of edible matter.

25. A composition according to claim 24, which is an edible fat product suitable as a bread spread, as a mayonnaise product, as a baking, cooking or frying product, as a dairy-based product, as a whipped product, as a salad oil, or as a pharmaceutical carrier.

26. A composition containing 10–99 wt. % of esters according to claim 24, the balance consisting of edible matter.

27. A composition containing 30–80 wt. % of esters according to claim 26, the balance consisting of edible matter.

28. A composition containing 0.5–99 wt. % of esters according to claim 16, the balance consisting of edible matter.

29. The composition of claim 8 comprising 10–99 wt. % of the esters.

* * * * *